(12) United States Patent
Hirano et al.

(10) Patent No.: US 10,317,330 B2
(45) Date of Patent: Jun. 11, 2019

(54) PARTICLE MEASURING APPARATUS

(71) Applicant: TOSHIBA MEMORY CORPORATION, Minato-ku, Tokyo (JP)

(72) Inventors: Masaki Hirano, Mie (JP); Yuichi Kuroda, Mie (JP)

(73) Assignee: TOSHIBA MEMORY CORPORATION, Tokyo (JP)

( * ) Notice: Subject to any disclaimer, the term of this patent is extended or adjusted under 35 U.S.C. 154(b) by 78 days.

(21) Appl. No.: 15/254,065

(22) Filed: Sep. 1, 2016

(65) Prior Publication Data

US 2017/0227443 A1  Aug. 10, 2017

(30) Foreign Application Priority Data

Feb. 9, 2016  (JP) .................. 2016-022649

(51) Int. Cl.
*G01N 15/00* (2006.01)
*G01N 15/14* (2006.01)
*G01N 15/06* (2006.01)
*G01N 21/53* (2006.01)
*G01N 15/02* (2006.01)

(52) U.S. Cl.
CPC ..... *G01N 15/1429* (2013.01); *G01N 15/0211* (2013.01); *G01N 15/06* (2013.01); *G01N 15/1436* (2013.01); *G01N 15/1459* (2013.01); *G01N 21/53* (2013.01); *G01N 2015/0046* (2013.01); *G01N 2015/0693* (2013.01); *G01N 2015/1486* (2013.01); *G01N 2201/06113* (2013.01); *G01N 2201/12* (2013.01)

(58) Field of Classification Search
None
See application file for complete search history.

(56) References Cited

U.S. PATENT DOCUMENTS

| | | | | |
|---|---|---|---|---|
| 2,438,865 A | * | 3/1948 | Rehard | F24H 1/102 392/489 |
| 3,790,760 A | * | 2/1974 | Stiller | G06M 1/101 356/335 |
| 4,286,140 A | * | 8/1981 | Dewulf | F24H 9/2014 165/156 |

(Continued)

FOREIGN PATENT DOCUMENTS

| JP | H11-183356 A | 7/1999 |
|---|---|---|
| JP | 2000-019095 A | 1/2000 |

(Continued)

*Primary Examiner* — Shawn Decenzo
(74) *Attorney, Agent, or Firm* — Foley & Lardner LLP

(57) ABSTRACT

A particle measuring apparatus includes a light source configured to irradiate a gas with light, a first optical detection unit configured to detect an intensity of reflected light from particles contained in the gas, and configured to output a first parameter value corresponding to the intensity of the reflected light, and a storage unit that stores first data indicating corresponding relationships between first parameter values particle components. The particle measuring apparatus further includes a calculation unit configured to compare the first parameter value transmitted from the first optical detection unit with the first data transmitted from the storage unit to determine a component of the particles contained in the gas.

4 Claims, 12 Drawing Sheets

(56) References Cited

U.S. PATENT DOCUMENTS

| | | | | |
|---|---|---|---|---|
| 4,521,521 A * | 6/1985 | Abbott | ............ | G01N 33/54313 |
| | | | | 250/574 |
| 5,275,787 A * | 1/1994 | Yuguchi | ................ | B01L 3/0268 |
| | | | | 209/579 |
| 5,418,108 A * | 5/1995 | Kmiecik-Lawrynowicz | ................ | |
| | | | | G03G 9/0804 |
| | | | | 430/137.14 |
| 5,529,701 A * | 6/1996 | Grisham | .................... | B01J 4/04 |
| | | | | 210/188 |
| 6,309,787 B1 * | 10/2001 | Cheng | ................ | G03G 9/09314 |
| | | | | 430/137.14 |
| 6,559,950 B1 * | 5/2003 | Dogariu | ................. | G01N 15/04 |
| | | | | 356/479 |
| 7,262,059 B2 * | 8/2007 | Zheng | ....................... | B01F 7/26 |
| | | | | 422/73 |
| 7,661,293 B2 * | 2/2010 | Dam | .................... | G01N 29/032 |
| | | | | 73/19.03 |
| 8,254,657 B2 * | 8/2012 | Pollack | ............. | G01N 15/1463 |
| | | | | 382/100 |
| 9,250,544 B2 * | 2/2016 | Kim | ....................... | G03F 7/7085 |
| 2017/0038290 A1 | 2/2017 | Nakai et al. | | |
| 2017/0157583 A1 * | 6/2017 | Kulkarni | ............. | G01N 15/065 |

FOREIGN PATENT DOCUMENTS

| | | |
|---|---|---|
| JP | 2005-283152 A | 10/2005 |
| JP | 2011-169884 A | 9/2011 |
| JP | 2014-002035 A | 1/2014 |
| JP | 2015-114230 A | 6/2015 |
| WO | WO 2015/156037 A1 | 10/2015 |

* cited by examiner

FIG. 3A

FIRST DATA

| PARTICLE COMPONENT | PARTICLE DIAMETER (nm) | DETECTED VOLTAGE (V) |
|---|---|---|
| A | 50 | ○○~△△ |
| A | 100 | △△~□□ |
| A | 150 | □□~ |
| : | : | : |
| B | 50 | ●●~▲▲ |
| B | 100 | ▲▲~■■ |
| B | 150 | ■■~ |
| : | : | : |
| C | 50 | ◎◎~△△ |
| C | 100 | △△~▥▥ |
| C | 150 | ▥▥~ |
| : | : | : |

SECOND DATA

FIG. 3B

| MEASUREMENT TIME | DETECTED VOLTAGE (V) |
|---|---|
| t1 | ○ |
| t2 | △ |
| t3 | 0 |
| t4 | 0 |
| t5 | ■ |
| t6 | 0 |
| t7 | ▲ |
| t8 | 0 |
| t9 | ◎ |
| t10 | 0 |
| : | : |

FIG. 5A

THIRD DATA

| PARTICLE COMPONENT | PARTICLE DIAMETER (nm) | DETECTED VOLTAGE (V) |
|---|---|---|
| A | 50 | x~y |
| A | 100 | y~z |
| A | 150 | z~ |
| : | : | : |
| B | 50 | xx~yy |
| B | 100 | yy~zz |
| B | 150 | zz~ |
| : | : | : |
| C | 50 | xxx~yyy |
| C | 100 | yyy~zzz |
| C | 150 | zzz~ |
| : | : | : |

FOURTH DATA

FIG. 5B

| MEASUREMENT TIME | DETECTED VOLTAGE (V) |
|---|---|
| t1 | x |
| t2 | y |
| t3 | 0 |
| t4 | 0 |
| t5 | xx |
| t6 | 0 |
| t7 | yy |
| t8 | 0 |
| t9 | xxx |
| t10 | 0 |
| : | : |

| PARTICLE COMPONENT | CONTACT ANGLE | DEGREE OF SUPERSATURATION FOR AGGREGATION | TEMPERATURE (°C) (115a) | TEMPERATURE (°C) (115b) |
|---|---|---|---|---|
| A | 20° | 1.2 | 40 | 10 |
| B | 40° | 1.4 | 50 | 20 |
| C | 80° | 2.5 | 60 | 20 |

FIRST DATA

PARTICLE MEASURING APPARATUS

CROSS-REFERENCE TO RELATED APPLICATION

This application claims the benefit of and priority to Japanese Patent Application No. 2016-022649; filed Feb. 9, 2016; the entire contents of which are incorporated herein by reference.

FIELD

Embodiments described herein relate generally to a particle measuring apparatus.

BACKGROUND

An optical particle measuring apparatus (particle counter) may be used so as to measure the number (hereinafter, also referred to as "particle count") of particles contained in a gas or a concentration (hereinafter, also referred to as "particle concentration") of the particles. The particle counter suctions a predetermined amount of an atmosphere from a measurement environment, and detects scattered light that occurs when irradiating the suctioned atmosphere with laser light to measure the number of particles or the particle concentration. In addition, a nuclear aggregation particle counter may be used so as to detect fine particles which are difficult to detect using an optical particle measuring apparatus. In the nuclear aggregation particle counter, a gas is allowed to pass through a gas flow passage, which enters a supersaturated state by using a condensate, and the condensate is condensed by using particles in a gas as a nucleus. According to this, the particles are detected after being enlarged.

However, in the above-described particle counter, functionality to perform particle component analysis is typically not included. A dedicated analysis apparatus (for example, gas chromatograph-mass spectrometer ("GC-MS")) is included separately from the particle counter so as to perform the particle component analysis. According to this, large-scaled facility is involved to perform the particle component analysis, and a long time is taken for the analysis.

SUMMARY

In some embodiments according to one aspect, a particle measuring apparatus includes a light source configured to irradiate a gas with light, a first optical detection unit configured to detect an intensity of reflected light from particles contained in the gas, and configured to output a first parameter value corresponding to the intensity of the reflected light, and a storage unit that stores first data indicating corresponding relationships between first parameter values particle components. The particle measuring apparatus further includes a calculation unit configured to compare the first parameter value transmitted from the first optical detection unit with the first data transmitted from the storage unit to determine a component of the particles contained in the gas.

In some embodiments according to another aspect, a particle measuring apparatus includes a first liquid-containing unit containing a liquid and provided at a periphery of a gas flow passage configured to allow a gas to pass, a temperature controller configured to control a temperature of the first liquid-containing unit, a first light source configured to irradiate the gas with light, a first optical detection unit configured to detect an intensity of reflected light from particles contained in the gas that passes through the first liquid-containing unit, and a first storage unit that stores first data indicating a corresponding relationship between an aggregation temperature at which the liquid aggregates with the particles, and a particle component. The particle measuring apparatus further includes a second storage unit that stores a number of particles or a particle concentration, which is detected in the first optical detection unit, of the particles contained in the gas, and a calculation unit configured to determine a component of the particles which are detected in the first optical detection unit based on the temperature of the first liquid-containing unit, the first data, and the number of particles or the particle concentration, and further configured to calculate the number of particles or the particle concentration.

In some embodiments according to another aspect, a particle measuring apparatus includes a liquid-containing unit containing a liquid and provided at a periphery of a gas flow passage configured to allow a gas to pass, a temperature controller configured to control a temperature of the liquid-containing unit, and a light source configured to irradiate the gas with light. The particle measuring apparatus further includes an optical detection unit configured to detect an intensity of reflected light from particles contained in the gas that passes through the liquid-containing unit, a storage unit that stores data indicating a corresponding relationship between an aggregation temperature at which the liquid aggregates with the particles, and a particle component, and a calculation unit configured to determine a component of the particles based on the temperature of the liquid-containing unit and the data stored in the storage unit.

Other aspects and embodiments of the disclosure are also encompassed. The foregoing summary and the following detailed description are not meant to restrict the disclosure to any particular embodiment but are merely meant to describe some embodiments of the disclosure.

BRIEF DESCRIPTION OF THE DRAWINGS

FIG. 3A and FIG. 3B illustrate a table illustrating an example of first and second data, and a table illustrating an example of a voltage value output from an optical detection unit, respectively.

FIG. 5A and FIG. 5B illustrate a table illustrating an example of third and fourth data, and a table illustrating an example of a voltage value output from an optical detection unit, respectively.

DETAILED DESCRIPTION

According to some embodiments, there is provided a particle measuring apparatus that is capable of measuring a number of particles or a particle concentration in a gas, and is capable of determining a component of the particles.

In general, according to some embodiments, there is provided a particle measuring apparatus including a light source that irradiates a gas with light. A first optical detection unit detects intensity of reflected light from particles contained in the gas, and outputs a first parameter value indicating the intensity of the reflected light. A storage unit stores first data indicating a corresponding relationship between the first parameter value and a component of the particles. A calculation unit compares the first parameter value transmitted from the first optical detection unit with the first data transmitted from the storage unit to determine a component of the particles contained in the gas.

Hereinafter, example embodiments will be described with reference to the accompanying drawings. The embodiments are not intended to be limiting.

In the description of some embodiments, the term "voltage value" may refer to a single value or a range of values. Comparing a first voltage value to a second voltage value may refer to comparing a first range of voltage values to a second range of voltage values, and one voltage value corresponding to or pertaining to another voltage value may refer to two voltage value ranges sharing a voltage value in common.

First Embodiment

Figure 1:
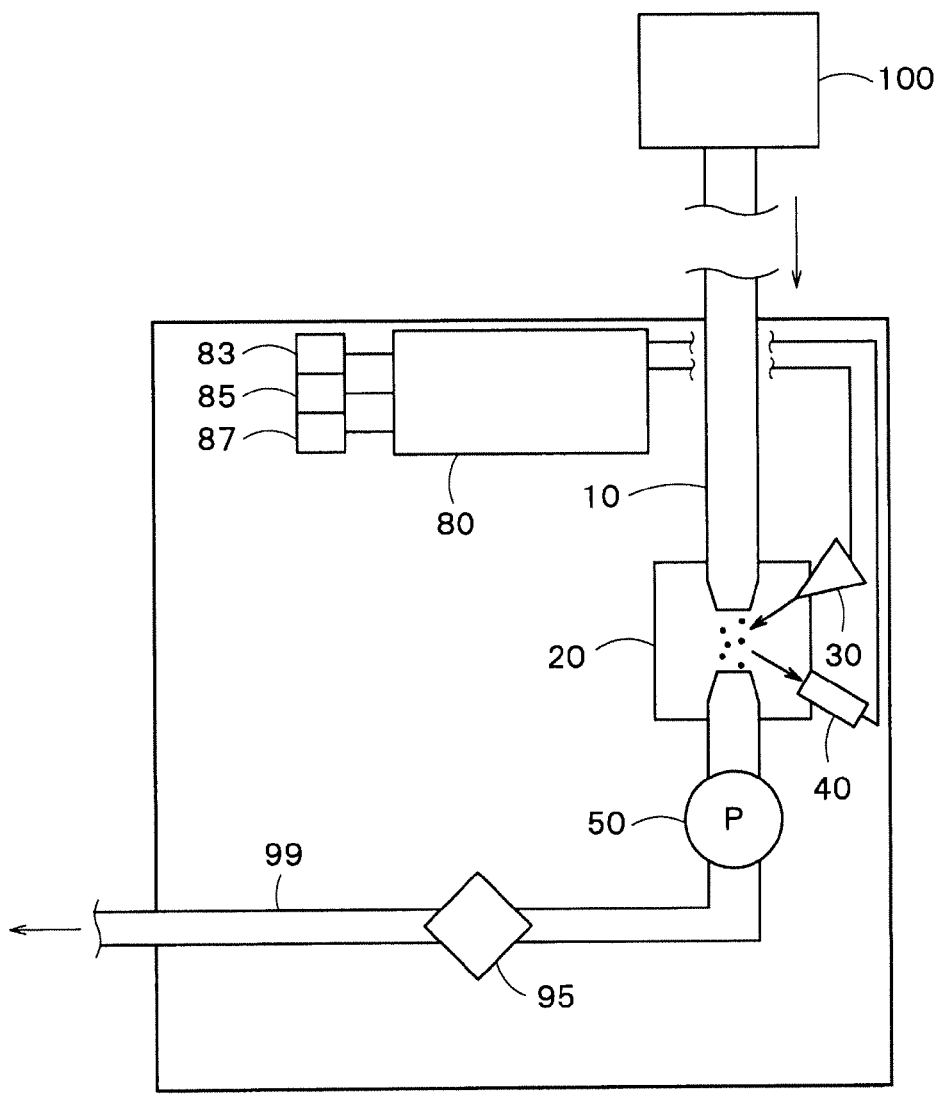
FIG. 1 is a block diagram illustrating an example of a configuration of a particle measuring apparatus according to a first embodiment.

FIG. 1 is a block diagram illustrating an example of a configuration of a particle measuring apparatus 1 according to a first example embodiment. The particle measuring apparatus 1 includes a gas supply unit 10, a measurement chamber 20, a light source 30, an optical detection unit 40, a pump 50, a calculation unit 80, a user interface 83, a storage unit 85, a display unit 87, a filter 95, and an exhaust tube 99.

The particle measuring apparatus 1 can obtain a gas from an environment 100 as a measurement object, and can measure a number of particles or a particle concentration which exist in the gas. That is, the particle measuring apparatus 1 may be a so-called particle counter. For example, the environment 100 as a measurement object may be an environment in a clean room that is used in a semiconductor manufacturing process, an environment in a chamber of a semiconductor manufacturing apparatus, or the like.

The gas supply unit 10 can be a tube that connects the environment 100 and the particle measuring apparatus 1, and introduces a gas for measurement (hereinafter, may be also referred to as a gas to be measured) in the environment 100 into the particle measuring apparatus 1. The gas in the environment 100 is suctioned by the pump 50, and is introduced to the gas supply unit 10 from the environment 100. The gas supply unit 10 transmits the introduced gas to the measurement chamber 20. For example, the gas to be measured may be air or a process gas that is used in a semiconductor manufacturing process.

The light source 30 is provided to the measurement chamber 20, and irradiates the gas to be measured with laser light. When particles, which exist in the gas to be measured, are irradiated with the laser light, the laser light is scattered (reflected) by the particles. A portion of the scattered light (reflected light) can be incident to the optical detection unit 40.

The optical detection unit (first optical detection unit) 40 is provided to the measurement chamber 20 and can receive the reflected light from the particles. The optical detection unit 40 detects the intensity of the reflected light from the particles in the gas to be measured. The optical detection unit 40 converts the intensity of the reflected light from the particles into a voltage (first parameter) to obtain a voltage value in accordance with the intensity of the reflected light. The voltage can be output as a first parameter value, with the first parameter value corresponding to a voltage or to a range of voltages of the optical detection unit 40. In addition, the optical detection unit 40 outputs the voltage value to the calculation unit 80. Alternatively or additionally, when the voltage value exceeds a predetermined threshold value, the optical detection unit 40 may output a signal indicating that the voltage value exceeds the threshold value.

The calculation unit 80 is electrically connected to the light source 30 and to the optical detection unit 40, and controls the light source 30 and the optical detection unit 40. In addition, the calculation unit 80 calculates or determines a number of particles, a particle concentration, a particle diameter, a particle component, or the like of particles in a gas to be measured based on information transmitted from the optical detection unit 40 and information transmitted from the storage unit 85. For example, the calculation unit 80 can measure a number of particles by counting the number of times at which the voltage value transmitted from the optical detection unit 40 exceeds the threshold value, or by counting signals indicating that the voltage value exceeds the threshold value.

For example, the calculation unit 80 may be a processor (e.g., a central processing unit ("CPU")) or the like. The processor may execute instructions stored in the storage unit 85, another memory, or another non-transitory computer readable storage medium. The calculation unit 80 generates laser light from the light source 30 for a period of time (e.g. a predetermined time), and obtains a number of particles from the voltage value that is measured in the optical detection unit 40 in synchronization with an operation of the light source 30. The gas to be measured flows in accordance with a suction flow rate, which is set in advance, of the pump 50. Accordingly, the calculation unit 80 can calculate a particle concentration (particle density) of particles contained in the gas to be measured based on the number of particles that is measured in a unit time, and the amount (volume) of the gas to be measured which flows per unit time.

The pump 50 suctions a gas from the gas supply unit 10 or the measurement chamber 20. When the pump 50 suctions the gas, the gas to be measured is introduced from the gas supply unit 10. A predetermined gas flow rate is useful for accurately measuring a number of particles in a gas. Accordingly, the pump 50 can be set to suction a gas in a flow rate equal to or greater than a defined flow rate that is specified for measuring the number of particles.

The user interface 83 is used to set and input measurement conditions by an operator. For example, the user interface 83 may be a data input device such as a keyboard, a mouse, and a touch panel.

The storage unit 85 stores first data indicating a corresponding relationship between a voltage range indicating the intensity of reflected light from a particle, and a particle component corresponding to the voltage range. In addition, the storage unit 85 stores second data indicating a corresponding relationship between the voltage range indicating the intensity of the reflected light from the particle, and a size (hereinafter, also referred to as "particle size") of the particles. In addition, the storage unit 85 stores a number of particles and a particle concentration which are measured in the optical detection unit 40. The first and second data may be input by an operator by using the user interface 83. Alternatively, the first and second data may be stored in the storage unit 85 in advance in a non-rewritable state. The first and second data may be alternatively be stored in the storage unit 85 in any other appropriate manner. The storage unit 85 may store data in any appropriate manner, including in one or more non-transitory computer-readable media.

The display unit 87 can display any of the first data, the second data, the number of particles, the particle concentration, or the like which are stored in the storage unit 85. For example, the display unit 87 may be a display, a touch panel, or the like. The user interface 83 and the display unit 87 may be the same touch panel.

The exhaust tube 99 is connected to the pump 50 and exhausts the gas to be measured, which passes through the pump 50, to an outer side of the particle measuring apparatus 1. The filter 95 is provided and can remove the particles from the gas to be measured.

Next, description will be given of an operation of the particle measuring apparatus 1.

Figure 2:
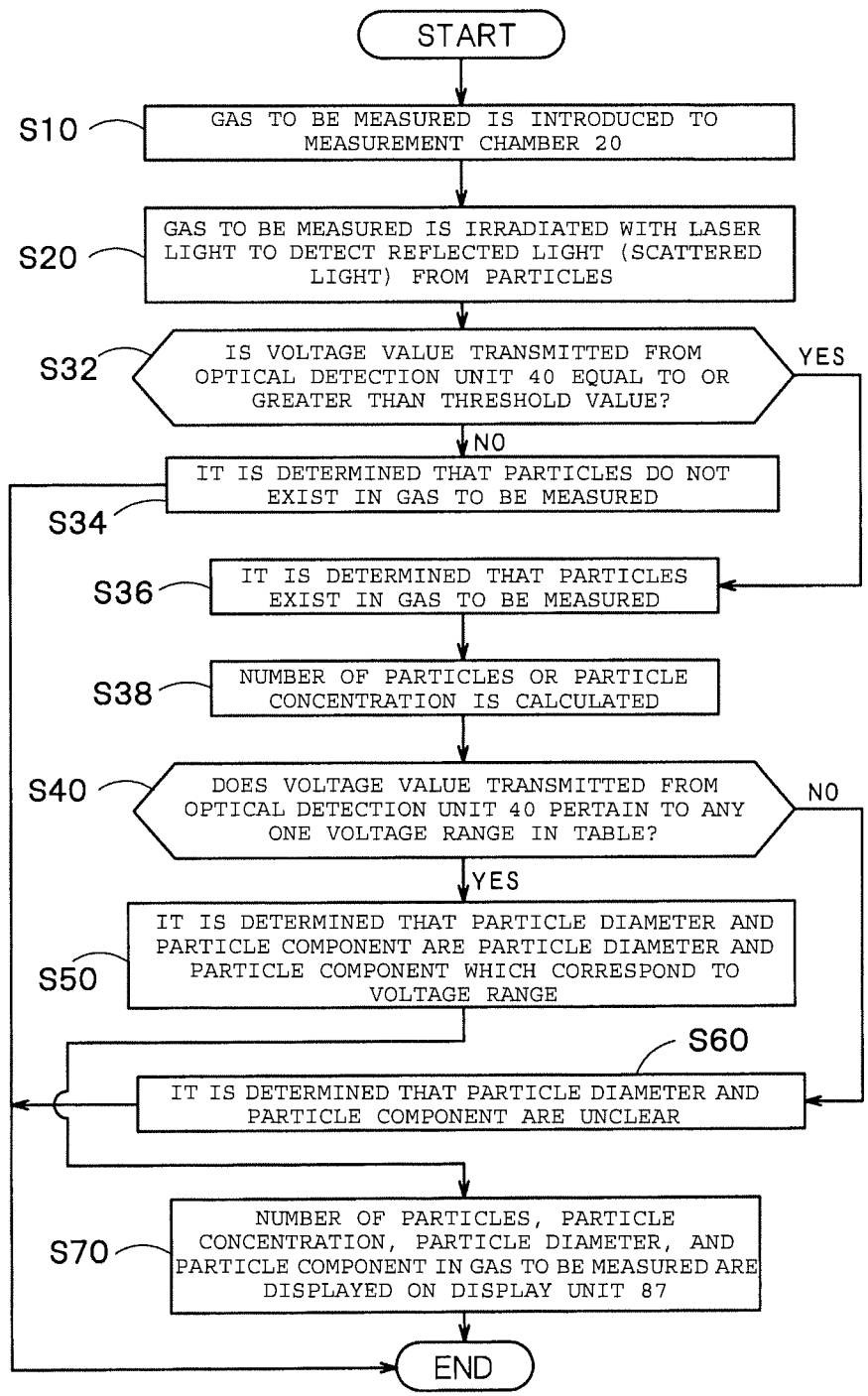
FIG. 2 is a flowchart illustrating an example of an operation of the particle measuring apparatus according to the first embodiment.

FIG. 2 is a flowchart illustrating an example of the operation of the particle measuring apparatus 1 according to the first example embodiment. First, the pump 50 suctions the gas to be measured from the environment 100. According to this, the gas to be measured passes through the gas supply unit 10, and is introduced to the measurement chamber 20 (S10).

Next, the light source 30 irradiates the gas to be measured with laser light, and the optical detection unit 40 detects reflected light (scattered light) that is reflected from particles in the gas to be measured (S20). The optical detection unit 40 outputs a voltage value corresponding to the intensity of the reflected light to the calculation unit 80.

Next, the calculation unit 80 receives the voltage value from the optical detection unit 40, and calculates a number of particles or a particle concentration in the gas to be measured. For example, the calculation unit 80 compares the voltage value transmitted from the optical detection unit 40, and a threshold value (S32). When the voltage value is less than the threshold value (NO in S32), the calculation unit 80 determines that particles do not exist in the gas to be measured at the comparison time (particles are not detected) (S34). On the other hand, when the voltage value becomes equal to or greater than the threshold value (YES in S32), the calculation unit 80 determines that particles exist in the gas to be measured (the particles are detected) at the comparison time (S36). In this case, the calculation unit 80 counts the particles as described above. The calculation unit 80 counts the particles per unit time, and calculates the number of particles or the particle concentration (S38).

In addition, when the particles are detected (S36), the calculation unit 80 compares the voltage value transmitted from the optical detection unit 40 with the first data (e.g., a table) and the second data (e.g., a table) which are stored in the storage unit 85 (S40). When the voltage value transmitted from the optical detection unit 40 pertains to any one voltage range in the table (YES in S40), the calculation unit 80 determines that the detected particles have a particle diameter and a particle component which correspond to the voltage range (S50). If the voltage value transmitted from the optical detection unit 40 pertains to a plurality of voltage ranges in the table, the calculation unit 80 determines that the particles in the gas to be measured have a particle diameter and a particle component which correspond to any one of the plurality of voltage ranges.

For example, FIG. 3A is a table illustrating an example of the first data (e.g., table) and the second data (e.g., table). The first data can include data indicating a corresponding relationship between the particle component and the voltage value, or data indicating a corresponding relationship between a first parameter value and a component of particles. The second data can include data indicating a corresponding relationship between the particle diameter and the voltage value, or data indicating a corresponding relationship between a first parameter value and a particle diameter. As illustrated in FIG. 3A, the first and second data may be stored as one table.

The voltage value (that is, intensity of the reflected light) transmitted from the optical detection unit 40 varies depending on a particle diameter (that is, a particle size). For example, if the particle size is large, the intensity of the reflected light becomes large. If the particle size is small, the intensity of the reflected light becomes small. Accordingly, similar to the second data illustrated in FIG. 3A, it is possible to specify the particle diameter to a certain extent based on the voltage value transmitted from the optical detection unit 40. In addition, the voltage value transmitted from the optical detection unit 40 also varies depending on the particle component. For example, the intensity of the reflected light varies in accordance with a physical value of particles such as a reflective index. Accordingly, similar to the first data illustrated in FIG. 3A, it is also possible to specify the particle component to a certain extent based on the voltage value transmitted from the optical detection unit 40. In addition, even in the same particle diameter and the same particle component, a voltage, which is actually output from the optical detection unit 40, varies to a certain extent. Accordingly, the voltage value in the first and second data can be set in a voltage range having a predetermined width.

The first and second data which indicate the above-described corresponding relationships may be created in advance and may be stored in the storage unit 85. The first data may be updated, for example, through the user interface 83. The calculation unit 80 compares the voltage value transmitted from the optical detection unit 40 and the voltage range of the first data to determine a particle diameter and a component (hereinafter, also referred to as "particle component") of particles contained in the gas to be measured.

FIG. 3B is a table illustrating an example of the voltage value that is measured in the optical detection unit 40 and is output from the optical detection unit 40. For example, the optical detection unit 40 periodically executes an operation of detecting reflected light. At this time, when particles do not exist in the gas to be measured, and the reflected light is hardly detected (t3, t4, t6, t8, t10, or the like), the voltage transmitted from the optical detection unit 40 becomes low (e.g. approximately 0 V). When particles exist in the gas to be measured, and the reflected light is detected (t2, t5, t7, t9, or the like), the voltage transmitted from the optical detection unit 40 becomes a voltage in accordance with the particle diameter and the component of the particles.

When the voltage value transmitted from the optical detection unit 40 does not pertain to any one voltage range in the table in FIG. 3A (NO in S40), the calculation unit 80 determines that the particle diameter and the component of the particles are unclear (S60).

Next, the calculation unit 80 displays a number of particles, a particle concentration, a particle diameter, a particle component, or the like of particles in the gas to be measured on the display unit 87 (S70). The calculation unit 80 may output any or all of information of the number of particles, the particle concentration, the particle diameter, and the particle component to the outside of the particle measuring apparatus 1. When a plurality of candidates for the particle diameter and the particle component exist, the calculation unit 80 may display or output any or all of the plurality of candidates for the particle diameter and the particle component. In addition, if the particle diameter and the particle component are unclear, the calculation unit 80 may display or output that the result is unclear. The gas to be measured is exhausted from the exhaust tube 99 to the outside of the particle measuring apparatus 1 through the filter 95.

As described above, the particle measuring apparatus 1 according to this embodiment stores the first data indicating a corresponding relationship between the voltage value transmitted from the optical detection unit 40 and the particle component, and the second data indicating a corresponding relationship between the voltage value transmitted from the optical detection unit 40 and the particle diameter in advance, and compares the voltage value corresponding to the reflected light detected by the optical detection unit 40 and the first and second data. According to this, the particle measuring apparatus 1 can determine the particle diameter and the particle component of particles contained in a gas. As a result, the particle measuring apparatus 1 can measure the number of particles or the particle concentration of the particles in the gas, and can also determine the particle diameter and the particle component of the particles.

Second Embodiment

Figure 4:
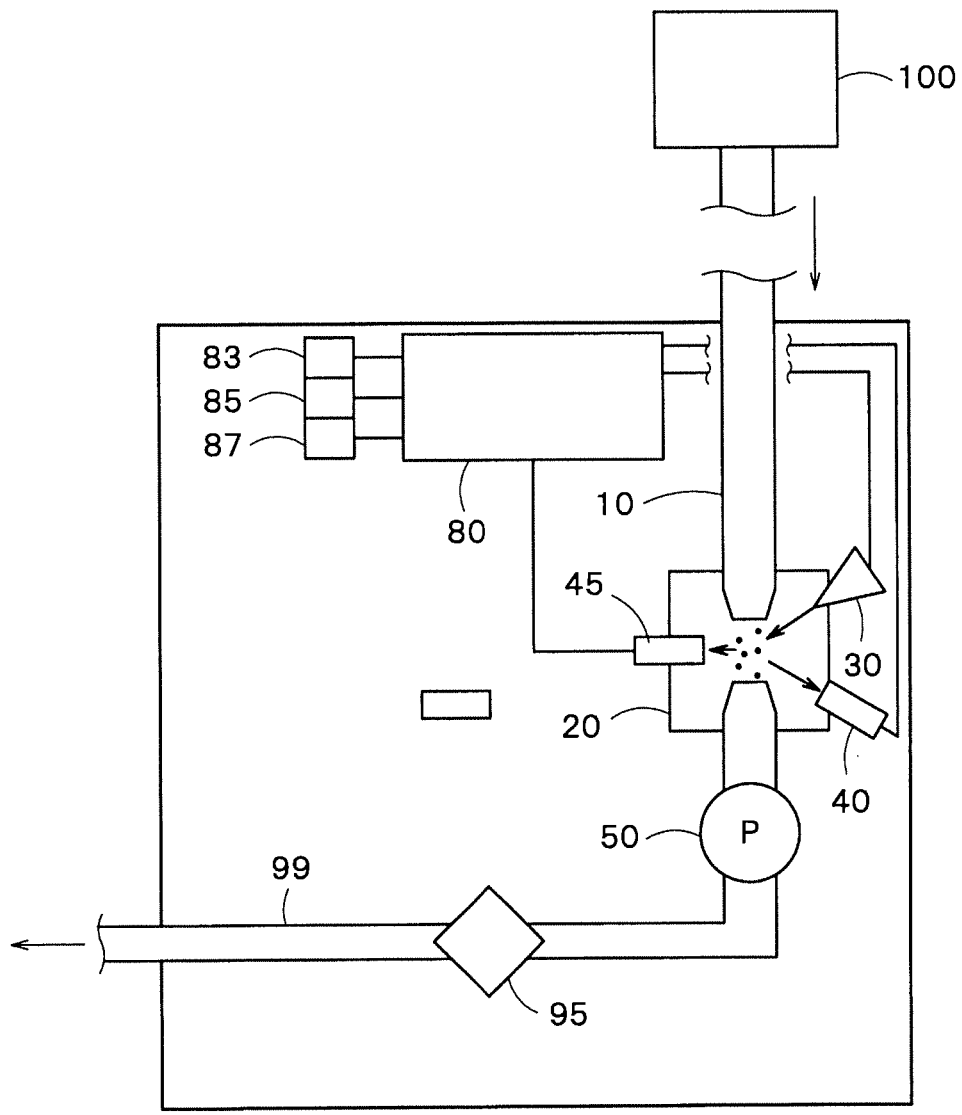
FIG. 4 is a block diagram illustrating an example of a configuration of a particle measuring apparatus according to a second embodiment.

FIG. 4 is a block diagram illustrating an example of a configuration of a particle measuring apparatus 2 according to a second example embodiment. The second example embodiment can be different from the first embodiment in some ways, including that a second optical detection unit 45 is further provided.

The optical detection unit (second optical detection unit) 45 detects intensity of reflected light from particles included in a gas from a direction different from a direction in the optical detection unit 40. The optical detection unit 45 converts the intensity of the reflected light from the particles into a voltage (e.g., relating to a second parameter) to obtain a voltage value in accordance with the intensity of the reflected light. In addition, the optical detection unit 45 outputs the voltage value to the calculation unit 80. The voltage can be output as a second parameter value, with the second parameter value corresponding to a voltage or to a range of voltages of the optical detection unit 45. Alternatively, when the voltage value exceeds a predetermined threshold value, the optical detection unit 45 may output a signal indicating that the voltage value exceeds the threshold value. The calculation unit 80 can measure a number of particles or a particle concentration of particles by counting the number of times at which the voltage value transmitted from the optical detection unit 45 exceeds the threshold value.

The storage unit 85 stores third data indicating a corresponding relationship between the voltage value transmitted from the optical detection unit 45 and a particle component. The third data is data in which the voltage range indicating the intensity of the reflected light and the particle component corresponding to the voltage range are made to correspond to each other. In addition, the storage unit 85 also stores data (fourth data) indicating a corresponding relationship between the voltage value transmitted from the optical detection unit 45 and the particle diameter (particle size). In addition, hereinafter, the first and second data, which are illustrated in FIG. 3A, are also referred to as a first table, and the third and fourth data, which are illustrated in FIG. 5A, are also referred to as a second table.

FIG. 5A is a table illustrating an example of the third and fourth data (e.g., second table). FIG. 5B is a table illustrating an example of a voltage value that is output from the optical detection unit 45. The second table and the first table illustrated in FIG. 3A are different from each other in terms of numerical value, but are the same kind of data, and thus detailed description of the second table will be omitted. In addition, the voltage value that is output from the optical detection unit 45, and the voltage value that is output from the optical detection unit 45 and is illustrated in FIG. 3B are different from each other in terms of numerical value, but are the same kind of data, and thus detailed description of the voltage value will be omitted.

In the first embodiment, the voltage value corresponding to the reflected light detected in the optical detection unit 40 is compared with the first table of the storage unit 85. However, when the voltage value transmitted from the optical detection unit 40 pertains to a plurality of voltage ranges in the first table and a plurality of particle diameters and components correspond to the voltage range, the calculation unit 80 may not determine a particle diameter and a component of particles.

Accordingly, the particle measuring apparatus 2 according to the second embodiment compares the voltage value corresponding to the reflected light detected in the optical detection unit 45 and the second table of the storage unit 85. The optical detection unit 45 detects the reflected light from a direction different from a direction in the optical detection unit 40, and thus the voltage value transmitted from the optical detection unit 45 is different from the voltage value transmitted from the optical detection unit 40. Accordingly, both the voltage value transmitted from the optical detection unit 40 and the voltage value transmitted from the optical detection unit 45 are used. Voltage values of the optical detection unit 40 (e.g., first parameter values) that correspond to a particle component or particle diameter may differ from voltage values of the optical detection unit 45 (e.g., second parameter values) that correspond to the same particle component or to the same particle diameter. Thus, the calculation unit 80 more accurately determines the particle diameter and the particle component.

Figure 6A:
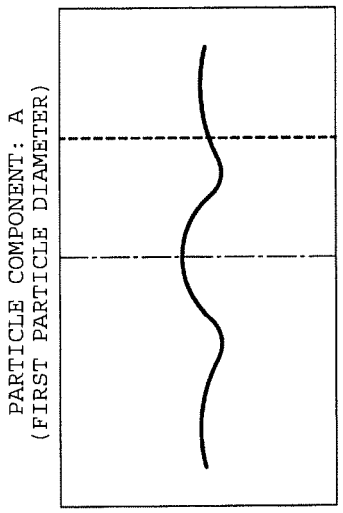
FIG. 6A, FIG. 6B, FIG. 6C, and FIG. 6D are graphs illustrating a relationship between intensity of reflected light and a scattering angle.
Figure 6B:
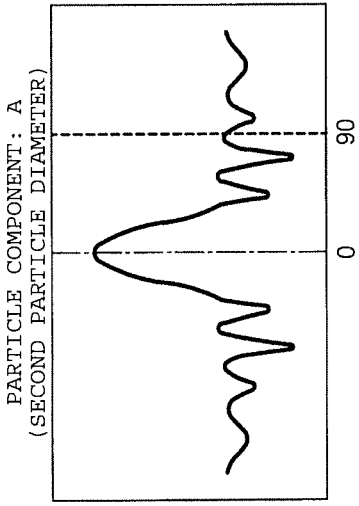
Figure 6C:
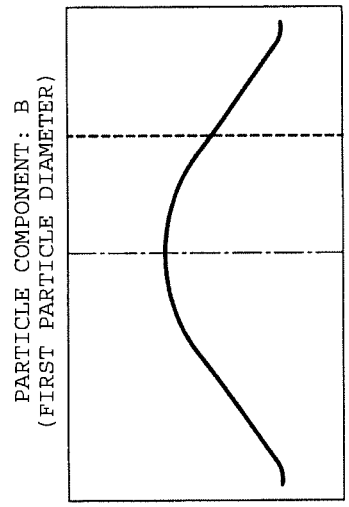
Figure 6D:
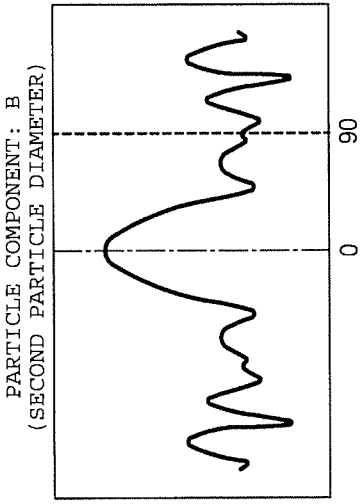

For example, FIGS. 6A to 6D are graphs illustrating a relationship between intensity (voltage value) of reflected light and a scattering angle (detection direction). The vertical axis of the graphs represents the intensity of reflected light, and the horizontal axis represents the scattering angle. FIG. 6A illustrates intensity of reflected light (intensity of scattered light) in a particle component A having a first particle diameter. FIG. 6B illustrates intensity of reflected light in the particle component A having a second particle diameter. FIG. 6C illustrates intensity of reflected light in a particle component B having the first particle diameter. FIG. 6D illustrates intensity of reflected light in the particle component B having the second particle diameter.

When referring to the graphs, it can be seen that even when the particle diameter or the particle component is the same, if the scattering angle (detection direction) is different, intensity of reflected light greatly varies. Accordingly, it can be seen that when detecting reflected light from a plurality of directions by using a plurality of the optical detection units 40 and 45, the particle diameter and the particle component can be specified. For example, the optical detection unit 40 detects reflected light from a direction in which the scattering angle is 0°. The optical detection unit 45 detects reflected light from a direction in which the scattering angle is 90°. According to this, even when one particle diameter and one particle component are not resolved with intensity (voltage value) of reflected light detected in the optical detection unit 40, the calculation unit 80 can specify the one particle diameter and the one particle component by further using the intensity (voltage value) of reflected light detected in the optical detection unit 45.

Of course, even when using voltage values transmitted from both of the optical detection units 40 and 45, one particle diameter and one particle component may not be specified in some cases. However, according to the second embodiment, it is possible to reduce a possibility of occurrence of the above-described cases.

In addition, a plurality of optical detection units, such as three or more optical detection units, may additionally or alternatively be used to detect reflected light from three or more different directions. According to this, it is possible to more accurately specify the particle diameter and the particle component. Additional optical detection units, and corresponding additional data and/or tables, can be provided in a manner similar to a manner in which the second optical detection unit 45, and corresponding additional data and/or tables, can be provided.

Figure 7:
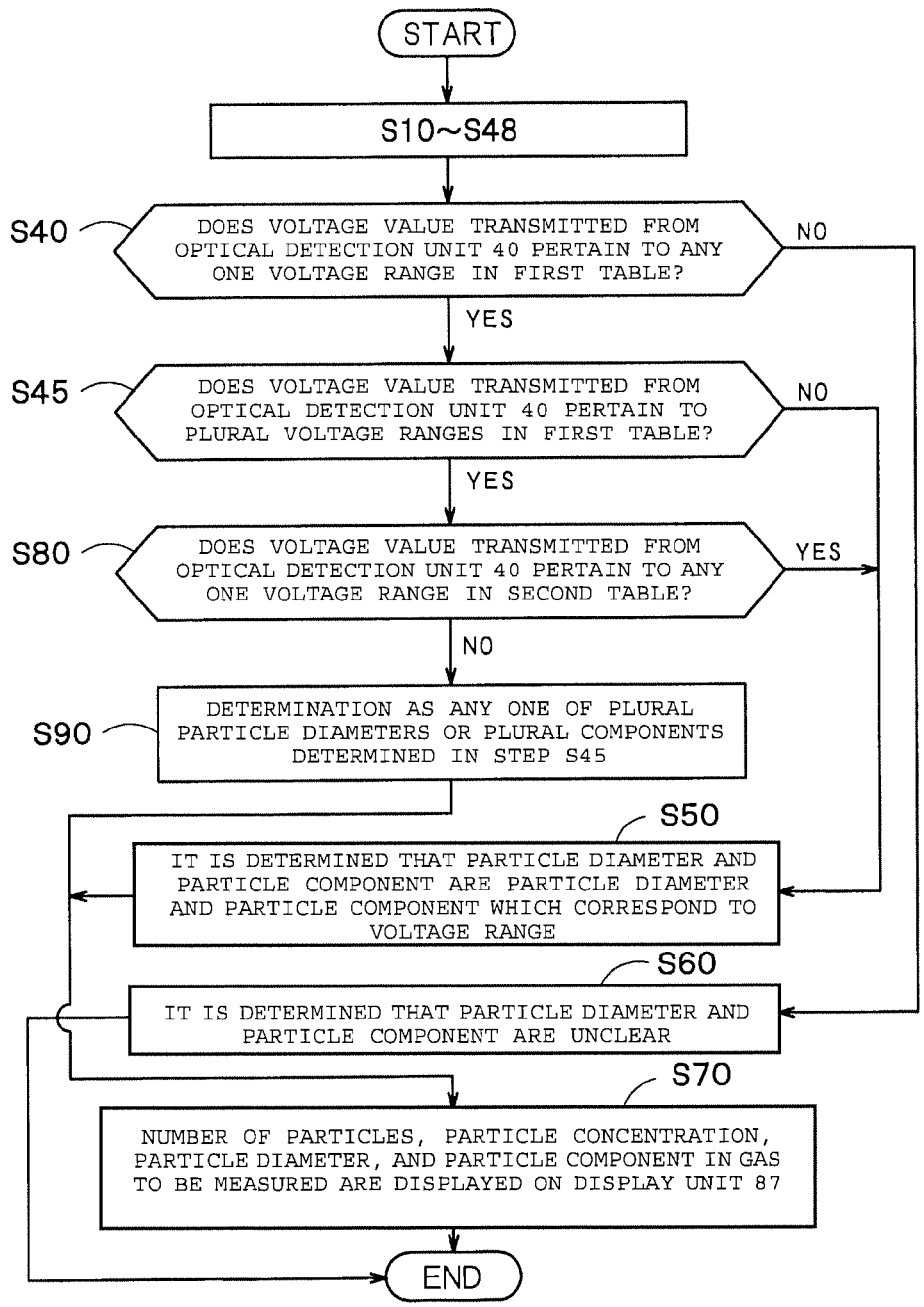
FIG. 7 is a flowchart illustrating an example of an operation of the particle measuring apparatus according to the second embodiment.

FIG. 7 is a flowchart illustrating an example of an operation of the particle measuring apparatus 2 according to the second embodiment. First, steps S10 to S40 are executed. In addition, in step S20, both of the optical detection units 40 and 45 detect reflected light (scattered light) that is reflected from particles in a gas to be measured. The optical detection units 40 and 45 output a voltage value corresponding to the intensity of the reflected light to the calculation unit 80. In addition, a number of particles or a particle concentration may be calculated by using one or more voltage values or ranges of voltage values transmitted from any one or both of the optical detection units 40 and 45.

In step S40, when the voltage value does not pertain to any one voltage range in the first table (NO in S40), the calculation unit 80 determines that a particle diameter and a particle component are unclear. However, in this case (NO in S40), it proceeds to step S80, and the calculation unit 80 may further compare the voltage value with the second table. When the voltage value does not pertain to any one of the first and second tables, the calculation unit 80 may determine that the particle diameter and the particle component are unclear (S60).

Next, the calculation unit 80 determines that the voltage value transmitted from the optical detection unit 40 pertains to a plurality of voltage ranges in the first table (first and second data) (S45). Here, when the voltage value transmitted from the optical detection unit 40 pertains to a single voltage range in the first table (NO in S45), the calculation unit 80 determines that the particle diameter and the particle component of the particles which are detected are a particle diameter and a particle component which correspond to the voltage range (S50).

On the other hand, when the voltage value transmitted from the optical detection unit 40 pertains to a plurality of the voltage ranges in the first table (YES in S45), the calculation unit 80 compares the voltage value transmitted from the optical detection unit 45 with the second table (third and fourth data) that is stored in the storage unit 85 (S80). When the voltage value transmitted from the optical detection unit 45 pertains to any one voltage range in the second table (YES in S80), the calculation unit 80 determines that the particle diameter and the particle component of the particles which are detected are a particle diameter and a particle component corresponding to the voltage range (S50). When the voltage value transmitted from the optical detection unit 45 does not pertain to anyone of the voltage ranges in the second table (NO in S80), the calculation unit 80 determines that the plurality of particle diameters or the plurality of particle components, which are determined in step S45, in the first table, are particle diameters and particle components of the particles which are detected (S90). In this case, alternatively, the calculation unit 80 may determine that the particle diameter and the particle component are unclear.

In addition, when the voltage value transmitted from the optical detection unit 45 pertains to a plurality of the voltage ranges in the second table, as is the case with "NO" in step S80, the calculation unit 80 may determine that the plurality of particle diameters or the plurality of particle components in the first and/or second tables are particle diameters and particle components of the particles which are detected. In this case, alternatively, the calculation unit 80 may determine that the particle diameter and the particle component are unclear.

Next, the calculation unit 80 displays a number of particles, a particle concentration, a particle diameter, and a particle component in a gas to be measured on the display unit 87 (S70). In step S90, when it is determined that particles have the plurality of particle diameters or the plurality of particle components in the first table, the calculation unit 80 may display the plurality of particle diameters or the plurality of particle components on the display unit 87. Information of the number of particles, the particle concentration, the particle diameters, and the particle component of the particles in the gas to be measured may be output to the outside of the particle measuring apparatus 2.

As described above, in the second embodiment, the reflected light is detected from a plurality of directions different from each other by using the plurality of optical detection units 40 and 45. The calculation unit 80 determines a particle diameter and a particle component of particles in a gas to be measured by using the voltage value transmitted from the optical detection unit 40, and the first table. In addition, when one particle diameter and one particle component are not resolved with the voltage value transmitted from the optical detection unit 40, the calculation unit 80 determines the particle diameter and the particle component of particles in a gas to be measured by using the voltage value transmitted from the optical detection unit 45 and the second table. According to this, the particle measuring apparatus 2 can more accurately determine the particle diameter or the particle component of particles contained in a gas.

Third Embodiment

Figure 8:
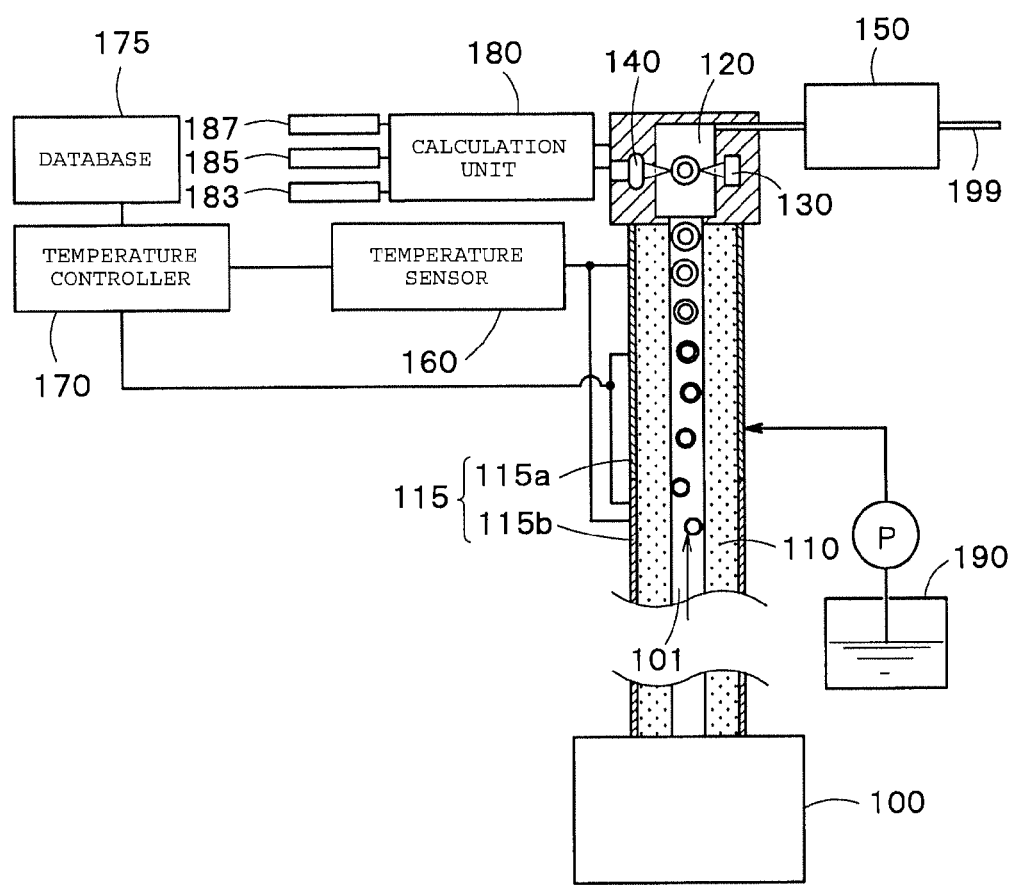
FIG. 8 is a view illustrating a configuration of a nuclear aggregation type particle measuring apparatus according to a third embodiment.

FIG. 8 is a view illustrating an example of a configuration of a nuclear aggregation type particle measuring apparatus 3 (hereinafter, referred to as "particle measuring apparatus 3") according to a third example embodiment. The particle measuring apparatus 3 includes a liquid-containing unit 110, a temperature adjustment tube 115, a measurement chamber 120, a light source 130, an optical detection unit 140, a pump 150, a temperature sensor 160, a temperature controller 170, a database 175, a calculation unit 180, a storage unit 185, a user interface 183, a display unit 187, a liquid supply unit 190, and an exhaust tube 199.

The particle measuring apparatus 3 allows a gas to be measured to pass through a gas flow passage 101 in which a liquid for aggregation is gasified into a supersaturation state. According to this, the liquid can condense by using fine particles in the gas to be measured as a nucleus (aggregation nucleus). According to this, for example, very small fine particles having a particle diameter of less than 100 nm grows (is enlarged) into particles on the order of µm. As described above, when the fine particles are enlarged, the optical detection unit 140 can more readily detect the fine particles.

The liquid-containing unit (first liquid-containing unit) 110 is provided at the periphery of the gas flow passage 101 through which the gas to be measured flows, and contains a liquid. The liquid-containing unit 110 is a porous member capable of containing a liquid, and may be, for example, a sponge or the like. The liquid is a liquid that can be gasified from the liquid-containing unit 110 and can exist in a saturated state in the gas flow passage 101, and can be condensed by using particles in the gas, such as particles to be detected, as a nucleus. For example, the liquid may be water, butanol or the like.

The temperature adjustment tube 115 is a tube at the periphery of the liquid-containing unit 110, and accommodates the liquid-containing unit 110. That is, the liquid-containing unit 110 is provided on an inner surface of the temperature adjustment tube 115, and the gas flow passage 101 is provided at the central portion of the liquid-containing unit 110. The temperature adjustment tube 115 is provided and can adjust a temperature of the liquid-containing unit 110. For example, a metal, glass, or the like is used for the temperature adjustment tube 115, and the temperature adjustment tube 115 can be provided with a heater (not illustrated) that adjusts an internal temperature of the temperature adjustment tube 115, or the like.

The temperature adjustment tube 115 includes an upper tube 115a (upper portion) and a lower tube 115b (lower portion). The upper tube 115a adjusts a temperature of an upper portion of the liquid-containing unit 110. The lower tube 115b adjusts a temperature of a lower portion of the liquid-containing unit 110. The temperature controller 170 can set the temperatures of the upper tube 115a and the lower tube 115b to temperatures different from each other.

The light source (first light source) 130 is provided to the measurement chamber 120, and irradiates the gas to be measured with laser light. The light source 130 may have a similar configuration as that of the light source 30 in FIG. 1. The optical detection unit (first optical detection unit) 140 is provided to the measurement chamber 120 to receive reflected light from particles, such as particles to be detected. The optical detection unit 140 may have a similar configuration as that of the optical detection unit 40 in FIG. 1. The pump 150 suctions a gas from the gas flow passage 101 or the measurement chamber 120. The pump 150 may have a similar configuration as that of the pump 50 in FIG. 1.

The temperature sensor 160 detects a temperature of the temperature adjustment tube 115, and outputs the temperature to the temperature controller 170. The temperature sensor 160 can individually detect temperatures of the upper tube 115a and the lower tube 115b of the temperature adjustment tube 115, respectively. According to this, the temperature sensor 160 can indirectly detect temperatures of the upper portion and the lower portion of the liquid-containing unit 110.

The temperature controller 170 controls a temperature of the temperature adjustment tube 115 and a temperature of the liquid-containing unit 110 in accordance with temperature conditions stored in the database 175. A measured value of the temperature of the temperature adjustment tube 115 is fed back from the temperature sensor 160 to the temperature controller 170, and thus the temperature controller 170 can control the temperature of the temperature adjustment tube 115 to be appropriate for the temperature conditions based on the measured value. In addition, the temperature controller 170 can control temperature of the upper tube 115a and the lower tube 115b of the temperature adjustment tube 115, respectively. According to this, the temperature controller 170 can indirectly control temperatures of the upper portion and the lower portion of the liquid-containing unit 110.

The database 175 as a first storage unit stores first data indicating a corresponding relationship between a temperature at which a liquid is condensed to particles, and a particle component. Here, a degree of supersaturation S, in which the liquid is condensed by using particles as a nucleus, is different depending on a particle component (for example, a contact angle of a liquid with respect to particles). Accordingly, a corresponding relationship between the aggregation temperature and the particle component can be expressed as a table. The database 175 stores the table as first data. This data can be stored in advance of a particle detection operation.

The storage unit 185 as the second storage unit stores a number of particles or a particle concentration which is detected in the optical detection unit 140. The storage unit 185 may store a voltage value transmitted from the optical detection unit 140.

The calculation unit 180 determines a particle component detected in the optical detection unit 140 based on the temperature of the liquid-containing unit 110 and the first data. In addition, the calculation unit 180 calculates a number of particles or a particle concentration of each particle component based on the number of particles or the particle concentration which is detected in the optical detection unit 140.

The user interface 183 may be similar to the user interface 83. An operator may register the first data in the database 175 through the user interface 183.

The display unit 187 displays any or all of the first data, second data, the number of particles or the particle concentration, or the like which are stored in the storage unit 185. The display unit 187 may have a similar configuration as that of the display unit 87.

The liquid supply unit 190 supplies a liquid to the liquid-containing unit 110. The liquid may be supplied from the liquid supply unit 190 to the liquid-containing unit 110 by a pump P. Alternatively, the liquid may be supplied from the liquid supply unit 190 to the liquid-containing unit 110 by using a capillary phenomenon, or in any other appropriate manner.

Figures 9, 10:
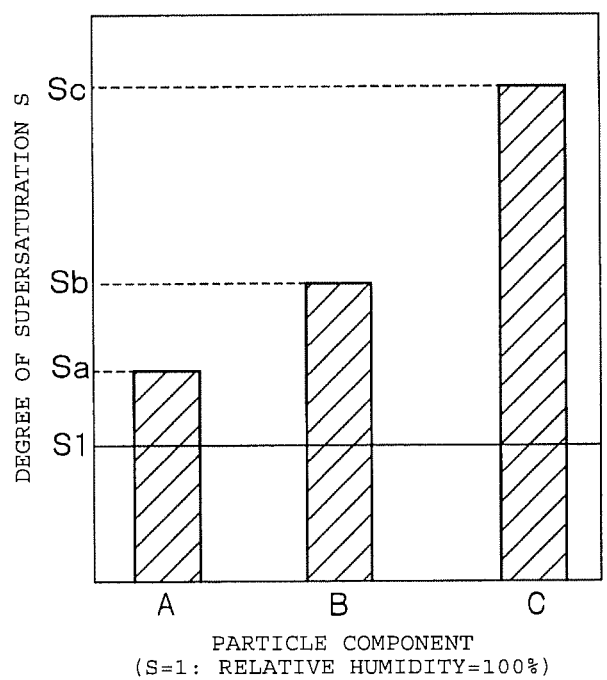
FIG. 9 is a graph illustrating a degree of supersaturation with respect to a particle component.
FIG. 10 is a table illustrating a corresponding relationship among a particle component, a liquid contact angle, a degree of supersaturation for aggregation, a temperature of a liquid-containing unit, and a temperature of a temperature adjustment tube.
Figure 11:
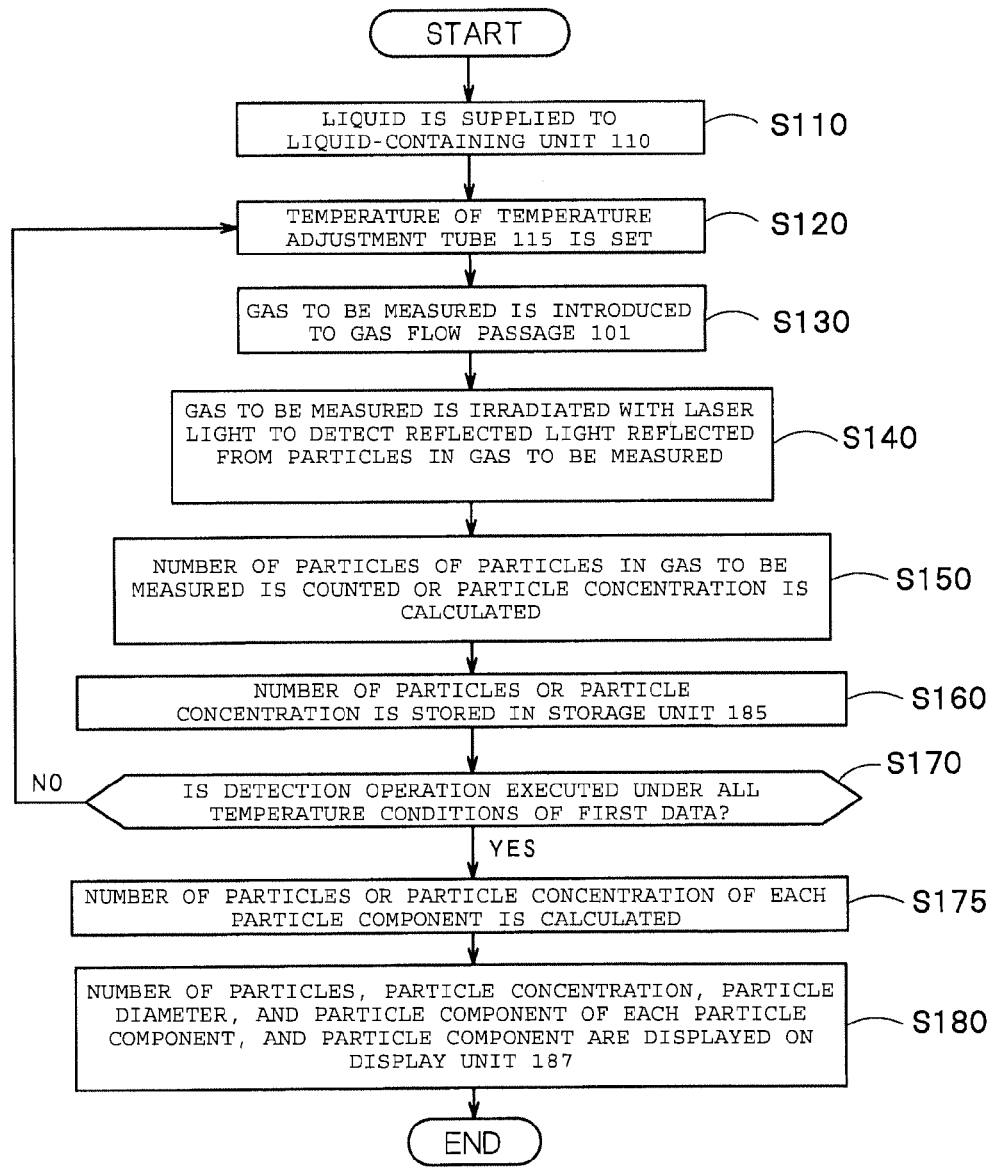
FIG. 11 is a flowchart illustrating an example of an operation of a particle measuring apparatus according to the third embodiment.

FIG. 9 is a graph illustrating the degree of supersaturation S with respect to a particle component. The vertical axis represents the degree of supersaturation S (hereinafter, also referred to as "degree of supersaturation for aggregation) that is involved for the liquid to be condensed by using particles as a nucleus. A degree of supersaturation S of 1 represents that relative humidity is 100%. The horizontal axis represents the particle component. For example, the ascending order of the degrees of supersaturation for aggregation S of particle components A to C are A, B, and C. A low degree of supersaturation for aggregation S represents that aggregation is likely to occur. In contrast, a high degree of supersaturation for aggregation S represents that aggregation is less likely to occur. Accordingly, a liquid is condensed to the particle component A at a relatively low degree of supersaturation S. In addition, the liquid is condensed to the particle component C at a relatively high degree of supersaturation S. A difference in the degree of supersaturation for concentration S occurs due to a difference in a contact angle among the particle components A to C as to be described with reference to FIG. 10. In addition, S1 in FIG. 9 represents that the degree of supersaturation S is 1 (relative humidity is 1000).

If it is desired to enlarge all of the particle components A to C, the degree of supersaturation S may be set to a level of Sc. According to this, the liquid is condensed by using the particle components A to C as a nucleus and grows in the gas flow passage 101. However, in this case, the optical detection unit 140 detects all of the particle components A to C, and thus discrimination between the particle components A to C may not performed.

Accordingly, the particle measuring apparatus 3 according to the third embodiment controls a particle component that becomes an aggregation nucleus of the liquid by changing the degree of supersaturation S of the gas flow passage 101. For example, when setting the degree of supersaturation S of the gas flow passage 101 as Sa, the particle component A becomes the aggregation nucleus of the liquid, but the particle components B and C do not become the aggregation nucleus of the liquid. Accordingly, the particle component A among the particle components A to C selectively grows and can be selectively detected. In addition, when the degree of supersaturation S of the gas flow passage 101 is set as Sb, the particle components A and B become the aggregation nucleus of the liquid, but the particle component C does not become the aggregation nucleus of the liquid. Accordingly, the particle components A and B among the particle components A to C selectively grow and can be selectively detected. In addition, when the degree of supersaturation S of the gas flow passage 101 is set as Sc, the particle components A to C become the aggregation nucleus of the liquid. Accordingly, all of the particle components A to C grow and can be detected. The calculation unit 180 can calculate the number of particles of each of the particle components A to C based on a difference in a number of particles that is detected in each of the degrees of supersaturation Sa to Sc. For example, it is assumed that a number of particles that is detected when the degree of supersaturation is Sa is set as Na, a number of particles that is detected when the degree of supersaturation is Sb is set as Nb, and a number of particles that is detected when the degree of supersaturation is Sc is set as Nc. In this case, Nc-Nb becomes a number of particles of the particle component C. Nb-Na becomes a number of particles of the particle component B. Na becomes a number of particles of the particle component A.

The degree of supersaturation S is controlled in accordance with the temperature of the liquid-containing unit 110 (indirectly, the temperature of the temperature adjustment tube 115). FIG. 10 is a table illustrating a corresponding relationship (first data) among the particle component, the contact angle of the liquid, the degree of supersaturation for aggregation, and the temperature of the liquid-containing unit 110 or the temperature of the temperature adjustment tube 115. In addition, the first data may include at least a corresponding relationship between the particle component and the temperature of the liquid-containing unit 110 or the temperature adjustment tube 115. It is not necessary that the contact angle of the liquid and the degree of supersaturation be included in the first data.

When referring to the first data, it can be seen that contact angles of the liquid with respect to the particle components A and B are different from each other depending on each component. According to this, degrees of supersaturation for aggregation of the particle components A and B are different from each other. So as to obtain this degree of supersaturation for aggregation, the temperature of the liquid-containing unit 110 or the temperature adjustment tube 115 is set with respect to each of the particle components A to C. For example, when detecting the particle component A in which the degree of supersaturation for aggregation is the smallest, the temperature of the upper tube **115*a* of the temperature adjustment tube 115 is set as approximately 40° C., and the temperature of the lower tube 115*b* is set as approximately 10° C. When detecting the particle components A and B, the temperature of the upper tube 115*a* of the temperature adjustment tube 115 is set as approximately 50° C., and the temperature of the lower tube 115*b* is set as approximately 20° C. When detecting all of the particle components A to C, the temperature of the upper tube 115*a* of the temperature adjustment tube 115 is set as approximately 60° C., and the temperature of the lower tube 115*b* is set as approximately 20° C. The reason why the temperature is different between the upper tube 115*a* and the lower tube 115*b*** as described above is because a supersaturation state can be more readily realized with the temperature variation. The temperatures described here are by way of example. Other appropriate temperatures can be set, including other appropriate temperatures that correspond to particle components to be detected.

The above-described first data can be registered in the database 175 in advance. Alternatively, or in combination, the first data is registered in the database 175 through the user interface 83.

Next, description will be given of an example operation of the particle measuring apparatus 3.

FIG. 11 is a flowchart illustrating an example of the operation of the particle measuring apparatus 3 according to the third embodiment. First, the liquid supply unit 190 supplies a liquid to the liquid-containing unit 110 (S110). The liquid-containing unit 110 suctions the liquid and contains the liquid.

Next, the temperature controller 170 sets the temperature of the temperature adjustment tube 115 with reference to the first data stored in the database 175 (S120). The temperature of the temperature adjustment tube 115 is set for the upper tube **115*a* and the lower tube 115*b*, respectively. At this time, the temperature sensor 160 feeds back a value, which is obtained by measuring the temperature of the temperature adjustment tube 115 and the liquid-containing unit 110, to the temperature controller 170. According to this, the temperature controller 170 can set the temperature of the temperature adjustment tube 115 and the liquid-containing unit 110 to a temperature in accordance with the first data with satisfactory accuracy. As described above with reference to FIG. 10, the temperature controller 170 sets the temperature of the liquid-containing unit 110 and the temperature adjustment tube 115** to a temperature corresponding to the degree of supersaturation for aggregation of any one of the particle components A to C which becomes an object or particle to be detected.

For example, first, the temperature controller 170 sets the temperature of the liquid-containing unit 110 and the temperature adjustment tube 115 to a temperature (first temperature) corresponding to the degree of supersaturation for aggregation Sa of the particle component A. That is, the temperature controller 170 sets the temperature of the upper tube 115a as approximately 40° C., and sets the temperature of the lower tube 115b as approximately 10° C.

Next, the pump 150 suctions the gas to be measured from the environment 100. According to this, the gas to be measured is introduced to the gas flow passage 101 (S130). The gas to be measured flows from the lower tube 115b toward the upper tube 115a. According to this, the gas to be measured reaches the temperature of the lower tube 115b, and then the temperature of the upper tube 115a. For example, in the above-described example, the temperature of the gas to be measured reaches approximately 10° C. when passing through the lower tube 115b and reaches approximately 40° C. when passing through the upper tube 115a. According to this, the liquid is condensed to the particle component A, and the particle component A is enlarged. On the other hand, the liquid is not condensed to the particle components B and C. Accordingly, the particle components B and C are not enlarged, and pass through the gas flow passage 101 with a particle diameter as is.

Next, the light source 130 irradiates the gas to be measured with laser light, and the optical detection unit 140 detects reflected light (scattered light) reflected from particles in the gas to be measured (S140). The optical detection unit 140 outputs a voltage value corresponding to the intensity of the reflected light to the calculation unit 180. Since the particle component A is enlarged, the optical detection unit 140 readily detects the particle component A, and outputs a voltage value corresponding to the intensity of the reflected light to the calculation unit 180. On the other hand, since the particle components B and C are not enlarged, the optical detection unit 140 does not obtain sufficiently great intensity of the reflected light from the particle components B and C, and thus the optical detection unit 140 hardly detects the particle components B and C. Even when the particle components B and C can be detected, a difference in reflection intensity is great between the particle component A, and the particle components B and C. Accordingly, it is possible to more readily discriminate the particle components B and C from the component A.

Next, the calculation unit 180 receives the voltage value transmitted from the optical detection unit 140, and counts particles in the gas to be measured or calculates a particle concentration (S150). At this time, the number of particles or the particle concentration which is calculated in the calculation unit 180 becomes a number of particles or a particle concentration of the particle component A. The number of particles or the particle concentration of the particle component A is stored in the storage unit 185 (S160). That is, the storage unit 185 stores the number of particles (first number of particles or first particle count) or the particle concentration (first particle concentration) which is detected when the temperature of the liquid-containing unit 110 is at the first temperature corresponding to the degree of supersaturation for aggregation Sa.

Next, the temperature controller 170 sets the temperature of the liquid-containing unit 110 and the temperature of the temperature adjustment tube 115 to a temperature (second temperature) corresponding to the degree of supersaturation for aggregation Sb of the particle component B (No in S170, S120). That is, the temperature controller 170 sets the temperature of the upper tube 115a as approximately 50° C., and sets the temperature of the lower tube 115b as approximately 20° C. Then, steps S130 to S160 are executed. According to this, the liquid is condensed to the particle components A and B, and the particle components A and B are enlarged. On the other hand, the liquid is not condensed to the particle component C. Accordingly, the particle component C is not enlarged, and passes through the gas flow passage 101 with a particle diameter as is.

Since the particle components A and B are enlarged, the optical detection unit 140 readily detects the particle components A and B, and outputs a voltage value corresponding to the intensity of reflected light from the particles A and B to the calculation unit 180. On the other hand, since the particle component C is not enlarged, the optical detection unit 140 does not obtain sufficiently great intensity of reflected light from the particle component C, and thus the optical detection unit 140 hardly detects the particle component C. Even when the particle component C can be detected, a difference in reflection intensity is great between the particle component C and the particle components A and B. Accordingly, it is possible to readily discriminate the particle component C from the particle components A and B.

The number of particles or the particle concentration which is calculated in the calculation unit 180 becomes the same as the number of particles or the particle concentration of the particle components A and B. The number of particles or the particle concentration of the particle components A and B are stored in the storage unit 185. That is, the storage unit 185 stores a number of particles (second number of particles or second particle count) or a particle concentration (second particle concentration) which is detected when the temperature of the liquid-containing unit 110 is at the second temperature corresponding to the degree of supersaturation for aggregation Sb.

Next, the temperature controller 170 sets the temperature of the liquid-containing unit 110 and the temperature of the temperature adjustment tube 115 to a temperature (third temperature) corresponding to the degree of supersaturation for aggregation Sc of the particle component C (NO in S170, S120). That is, the temperature controller 170 sets the temperature of the upper tube 115a as approximately 60° C., and sets the temperature of the lower tube 115b as approximately 20° C. In addition, steps S130 to S160 are executed again. According to this, a liquid is condensed to the particle components A to C, and the particle components A to C are enlarged. Since the particle components A to C are enlarged, the optical detection unit 140 readily detects all of the particle components A to C, and outputs a voltage value corresponding to intensity of reflected light to the calculation unit 180.

The number of particles or the particle concentration which is calculated in the calculation unit 180 becomes a number of particles or a particle concentration of the particle components A to C. The number of particles or the particle concentration of the particle components A to C are stored in the storage unit 185. That is, the storage unit 185 stores a number of particles (third number of particles or third particle count) or a particle concentration (third particle concentration) which is detected when the liquid-containing unit 110 is at the third temperature corresponding to the degree of supersaturation for aggregation Sc.

When the first data further includes another temperature condition (NO in S170), the temperature controller 170 sets the temperature of the liquid-containing unit 110 and temperature of the temperature adjustment tube 115 to another temperature, and repeats step S130 to S160. As described above, the particle measuring apparatus 3 counts the number of particles or calculates the particle concentration while changing the temperature of the liquid-containing unit 110 and temperature of the temperature adjustment tube 115.

When a detection operation is executed with respect to all temperature conditions of the first data (YES in S170), as described above, the calculation unit 180 calculates the number of particles or the particle concentration of each of the particle components (S175). For example, a first number of particles, which is detected when the degree of supersaturation for aggregation of the gas flow passage 101 is Sa, is set as Na, a second number of particles, which is detected when the degree of supersaturation for aggregation of the gas flow passage 101 is Sb, is set as Nb, and a third number of particles, which is detected when the degree of supersaturation for aggregation of the gas flow passage 101 is Sc, is set as Nc. In this case, the calculation unit 180 determines Na as a number of particles of the particle component A. The calculation unit 180 determines a difference (Nb-Na) between the first number of particles Na and the second number particles Nb as a number of particles of the particle component B. The calculation unit 180 determines a difference (Nc-Nb) between the second number of particles Nb and the third number of particles Nc as a number of particles of the particle component C. In addition, the calculation unit 180 can calculate the particle concentration in the same manner. For example, a first particle concentration, which is detected when the degree of supersaturation for aggregation of the gas flow passage 101 is Sa, is set as Ca, a second particle concentration, which is detected when the degree of supersaturation for aggregation of the gas flow passage 101 is Sb, is set as Cb, and a third particle concentration, which is detected when the degree of supersaturation for aggregation of the gas flow passage 101 is Sc, is set as Cc. In this case, the calculation unit 180 determines Ca as a particle concentration of the particle component A. The calculation unit 180 determines a difference (Cb-Ca) between the first particle concentration Ca and the second particle concentration Cb as a particle concentration of the particle component B. The calculation unit 180 determines a difference (Cc-Cb) between the second particle concentration Cb and the third particle concentration Cc as a particle concentration of the particle component C.

Next, the calculation unit 180 displays the numbers of particles, the particle concentrations, the particle diameters of the particle components A to C, and the particle components on the display unit 187 (S180). The calculation unit 180 may output information of the numbers of particles, the particle concentrations, the particle diameters, and the particle components of the particle components A to C to the outside of the particle measuring apparatus 3. The gas to be measured is exhausted from the exhaust tube 199 to the outside of the particle measuring apparatus 3.

As described above, the particle measuring apparatus 3 according to the third embodiment performs detection after selectively enlarging particles by setting the temperature of the liquid-containing unit 110 and the temperature of the temperature adjustment tube 115 to a plurality of temperatures based on a corresponding relationship between a condensation temperature of a liquid and a particle component. According to this, the particle measuring apparatus 3 can obtain a number of particles or a particle concentration for each particle component.

Fourth Embodiment

Figure 12:
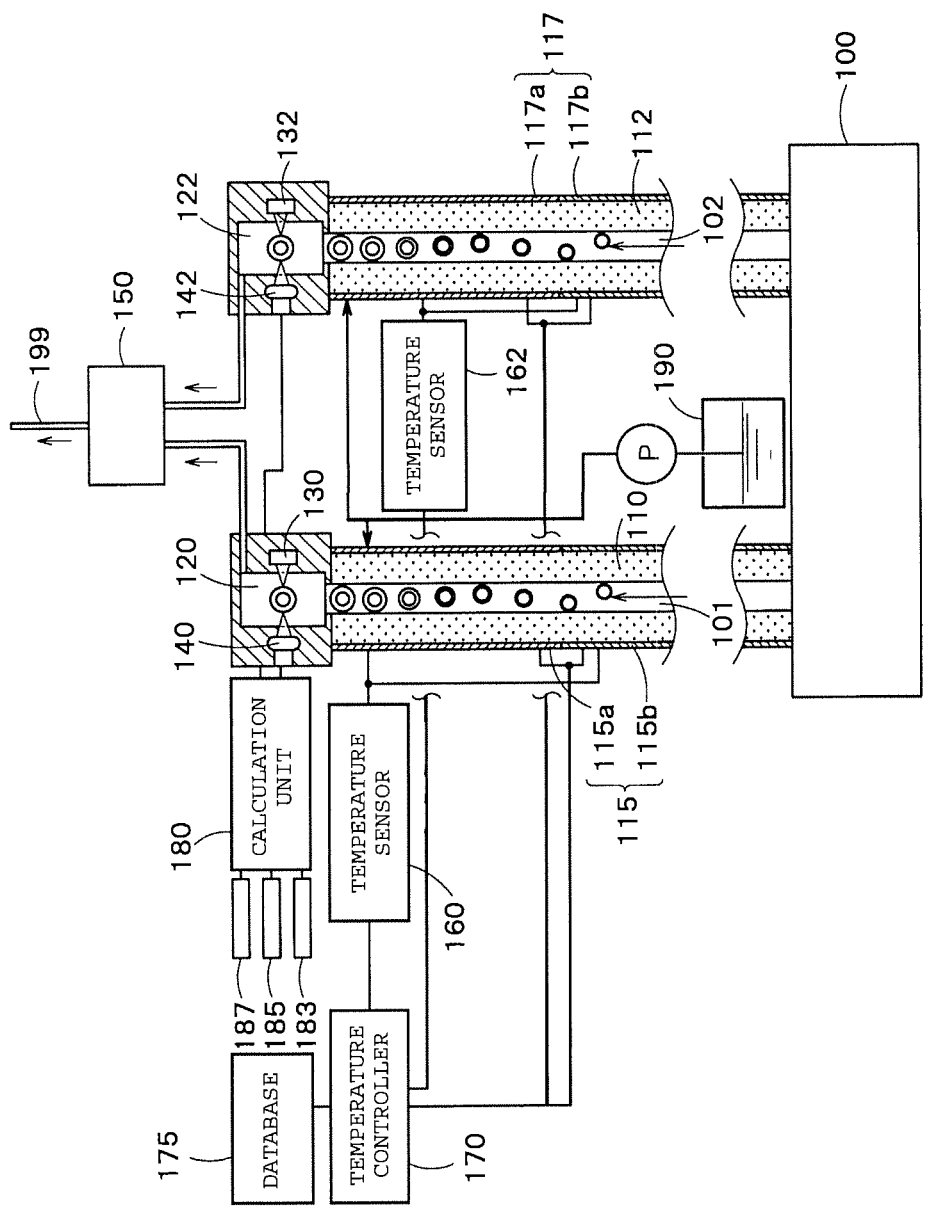
FIG. 12 is a view illustrating an example of a configuration of a nuclear aggregation type particle measuring apparatus according to a fourth embodiment.

FIG. 12 is a view illustrating an example of a configuration of a nuclear aggregation type particle measuring apparatus 4 (hereinafter, referred to as "particle measuring apparatus 4") according to a fourth example embodiment. The particle measuring apparatus 4 can differ from the particle measuring apparatus 3 according to the third embodiment in some ways, such as that a second liquid-containing unit 112, a second temperature adjustment tube 117, a second measurement chamber 122, a second light source 132, a second optical detection unit 142, and a second temperature sensor 162 are further provided. The other configurations or components in the fourth embodiment may be similar to corresponding configurations or components in the third embodiment. Accordingly, a plurality of the liquid-containing units, a plurality of the temperature adjustment tubes, a plurality of the measurement chambers, a plurality of the light sources, a plurality of the optical detection units, and a plurality of the temperature sensors are provided, and the other configuring elements may be common to the third embodiment.

The second liquid-containing unit 112 is provided at a periphery of a gas flow passage 102 different from the gas flow passage 101, and contains a liquid. The gas flow passages 101 and 102 are connected to the same environment 100, and allow a gas to be measured from the environment 100 to flow. As is the case with a first liquid-containing unit 110, the second liquid-containing unit 112 is a porous member capable of containing a liquid, and may be, for example, a sponge or the like. The liquid can be gasified from the second liquid-containing unit 112 to exist in a saturated state in the gas flow passage 102, and can be condensed by using particles in a gas as a nucleus. The liquid is similar to the liquid that is contained in a first liquid-containing unit 110, and may be, for example, water, butanol or the like.

The second temperature adjustment tube 117 is provided at the periphery of the second liquid-containing unit 112, and accommodates the second liquid-containing unit 112. That is, the second liquid-containing unit 112 is provided on an inner surface of the second temperature adjustment tube 117, and the gas flow passage 102 is provided at the central portion of the second liquid-containing unit 112. The second temperature adjustment tube 117 is provided and can adjust a temperature of the second liquid-containing unit 112. For example, a metal, glass, or the like is used for the second temperature adjustment tube 117.

The second temperature adjustment tube 117 includes an upper tube 117a and a lower tube 117b. The upper tube 117a adjusts a temperature of an upper portion of the second liquid-containing unit 112. The lower tube 117b adjusts a temperature of a lower portion of the second liquid-containing unit 112. The temperature controller 170 can set the temperatures of the upper tube 117a and the lower tube 117b to temperatures different from each other. In addition, the temperature controller 170 controls a temperature of the second temperature adjustment tube 117 individually from a first temperature adjustment tube 115. Accordingly, respective temperatures of the upper tubes 115a and 117a, and the lower tubes 115b and 117b can be individually controlled.

The second light source 132 is provided to the second measurement chamber 122, and irradiates a gas to be measured with laser light. A configuration of the second light source 132 may be similar to that of a first light source 130.

The second optical detection unit 142 is provided to the second measurement chamber 122 to receive reflected light from particles. The second optical detection unit 142 detects intensity of the reflected light from the particles in the gas to be measured in the second measurement chamber 122. A configuration of the second optical detection unit 142 may be similar to that of a first optical detection unit 40. The calculation unit 180 measures a number of particles (first number of particles or first particle count) of particles in a first measurement chamber 120 based on a voltage value transmitted from a first optical detection unit 140, and measures a number of particles (second number of particles or second particle count) of particles in the second measurement chamber 122 based on a voltage value transmitted from the second optical detection unit 142. The first number of particles and the second number of particles are stored in the storage unit 185 in combination with the voltage values.

The second temperature sensor 162 detects the temperature of the second temperature adjustment tube 117 and the temperature of the second liquid-containing unit 112, and outputs the temperatures to the temperature controller 170. The second temperature sensor 162 can detect temperatures of the upper tube 117a and the lower tube 117b of the second temperature adjustment tube 117, respectively. According to this, the second temperature sensor 162 can detect a temperature of an upper portion and a temperature of a lower portion of the second liquid-containing unit 112.

The temperature controller 170 controls the temperatures of the first and second temperature adjustment tubes 115 and 117, and the temperatures of the first and second liquid-containing units 110 and 112 in accordance with temperature conditions stored in the database 175. Measured values of the temperatures of the first and second temperature adjustment tubes 115 and 117, and the first and second liquid-containing units 110 and 112 are fed back from the first and second temperature sensors 160 and 162 to the temperature controller 170. Accordingly, the temperature controller 170 controls the temperatures of the first and second temperature adjustment tubes 115 and 117, and the first and second liquid-containing units 110 and 112 to be suitable for the temperature conditions based on the measured values.

As is the case with the third embodiment, the database 175 can store the first data in advance.

The storage unit 185 stores a first number of particles or a first particle concentration which is detected in the first optical detection unit 140, and also stores a second number of particles or a second particle concentration which is detected in the second optical detection unit 142.

The calculation unit 180 determines a particle component detected in each of the first and second optical detection units 140 and 142 based on respective temperatures of the first and second liquid-containing units 110 and 112 and the first data. In addition, the calculation unit 180 calculates a number of particles or a particle concentration of each particle component, which exists in the first and second measurement chambers 120 and 122, based on the number of particles or the particle concentration which is detected in the first and second optical detection units 140 and 142.

The user interface 183 and the display unit 187 may be similar to those in the third embodiment. The liquid supply unit 190 supplies a liquid commonly to the first and second liquid-containing units 110 and 112.

Next, description will be given of an operation of the particle measuring apparatus 4.

Figure 13:
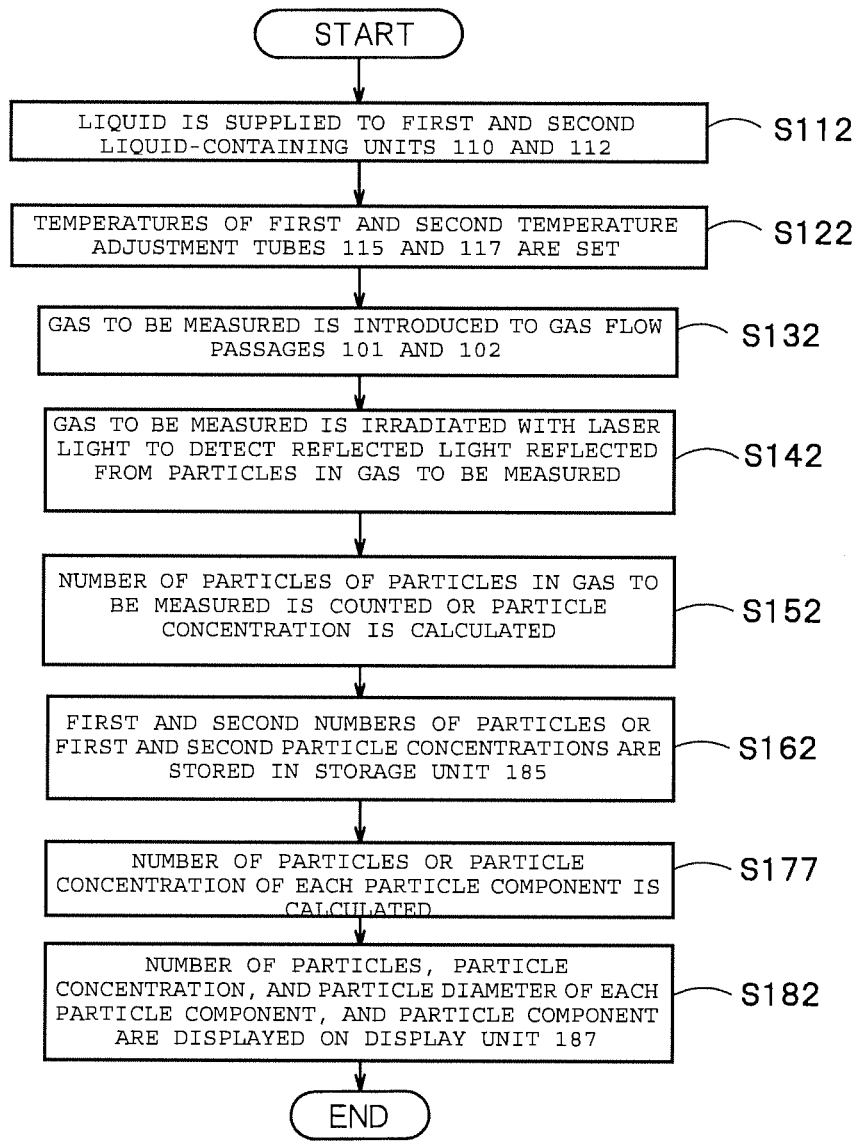
FIG. 13 is a flowchart illustrating an example of an operation of the particle measuring apparatus according to the fourth embodiment.

FIG. 13 is a flowchart illustrating an example of the operation of the particle measuring apparatus 4 according to the fourth embodiment. First, the liquid supply unit 190 supplies a liquid to the first and second liquid-containing units 110 and 112 (S112). The first and second liquid-containing units 110 and 112 suction the liquid and contain the liquid.

Next, the temperature controller 170 sets the temperatures of the first and second temperature adjustment tubes 115 and 117 with reference to the first data stored in the database 175 (S122). The temperature of the first temperature adjustment tube 115 is individually set in the upper tube 115a and the lower tube 115b. The temperature of the second temperature adjustment tube 117 is individually set in the upper tube 117a and the lower tube 117b.

For example, the temperature controller 170 sets the temperature of the first liquid-containing unit 110 and the temperature of the first temperature adjustment tube 115 to a temperature (first temperature) corresponding to the degree of supersaturation for aggregation Sa of the particle component A. That is, the temperature controller 170 sets the temperature of the upper tube 115a as approximately 40° C., and sets the temperature of the lower tube 115b as approximately 10° C. On the other hand, the temperature controller 170 sets the temperature of the second liquid-containing unit 112 and the temperature of the second temperature adjustment tube 117 to a temperature (second temperature) corresponding to the degree of supersaturation for aggregation Sb of the particle component B. That is, the temperature controller 170 sets the temperature of the upper tube 117a as approximately 50° C., and sets the temperature of the lower tube 117b as approximately 20° C. According to this, the gas flow passages 101 and 102 are set to degrees of supersaturation which are different from each other.

Next, the pump 150 suctions the gas to be measured from the environment 100. According to this, the gas to be measured is introduced to the gas flow passages 101 and 102 (S132). The gas to be measured flows from the lower tube 115b toward the upper tube 115a, and flows from the lower tube 117b toward the upper tube 117a in combination of (simultaneously with) the above-described flowing. According to this, the gas to be measured reaches the temperature of the lower tube 115b, and then the temperature of the upper tube 115a in the gas flow passage 101. In addition, the gas to be measured reaches the lower tube 117b and then the temperature of the upper tube 117a in the gas flow passage 102. According to this, in the gas flow passage 101, a liquid is condensed to the particle component A, and the particle component A is enlarged. In the gas flow passage 101, the liquid is not condensed to the particle components B and C. On the other hand, in the gas flow passage 102, the liquid is condensed to the particle components A and B, and the particle components A and B are enlarged. In the gas flow passage 102, the liquid is not condensed to the particle component C.

Next, the first and second light sources 130 and 132 irradiate the gas to be measured with laser light, and first and second optical detection units 140 and 142 detect reflected light (scattered light) reflected from particles in the gas to be measured (S142). The first optical detection unit 140 readily detects the particle component A, and outputs a voltage value corresponding to intensity of the reflected light to the calculation unit 180. However, the first optical detection unit 140 hardly detects the particle components B and C. Even when the particle components B and C can be detected, a difference in reflection intensity is great between the particle component A, and the particle components B and C. Accordingly, it is possible to readily discriminate the particle components B and C from the particle component A. The second optical detection unit 142 readily detects the particle components A and B, and outputs a voltage value corresponding to intensity of reflected light from the particle components A and B to the calculation unit 180. However, the second optical detection unit 142 hardly detects the particle component C. Even when the particle component C can be detected, a difference in reflection intensity is great between the particle components A and B, and the particle component C. Accordingly, it is possible to readily discriminate the particle component C from the particle components A and B.

Next, the calculation unit 180 receives the voltage values from the first and second optical detection units 140 and 142, and counts a number of particles in the gas to be measured or calculates a particle concentration of the particles (S152). At this time, the calculation unit 180 calculates a first number of particles or a first particle concentration of the particle component A by using a voltage value transmitted from the first optical detection unit 140. The calculation unit 180 calculates a second number of particles or a second particle concentration of the particle components A and B by using a voltage value transmitted from the second optical detection unit 142. The first and second numbers of particles, or the first and second particle concentrations are stored in the storage unit 185 (S162). As described above, the storage unit 185 stores the first number of particles or the first particle concentration which is detected when the temperature of the liquid-containing unit 110 is at a first temperature corresponding to the degree of supersaturation for aggregation Sa, and the second number of particles or the second particle concentration which is detected when the temperature of the liquid-containing unit 112 is at a second temperature corresponding to the degree of supersaturation for aggregation Sb.

Next, the calculation unit 180 calculates a number of particles or a particle concentration of each particle component (S177). For example, a first number of particles, which is detected when the degree of supersaturation for aggregation of the gas flow passage 101 is Sa, is set as Na, and a second number of particles, which is detected when the degree of supersaturation for aggregation of the gas flow passage 102 is Sb, is set as Nb. In this case, the calculation unit 180 determines Na as a number of particles of the particle component A. The calculation unit 180 determines a difference (Nb-Na) between the first number of particles Na and the second number of particles Nb as a number of particles of the particle component B. In addition, the calculation unit 180 can calculate the particle concentration in the same manner. For example, a first particle concentration, which is detected when the degree of supersaturation for aggregation of the gas flow passage 101 is Sa, is set as Ca, and a second particle concentration, which is detected when the degree of supersaturation for aggregation of the gas flow passage 102 is Sb, is set as Cb. In this case, the calculation unit 180 determines Ca as a particle concentration of the particle component A. The calculation unit 180 determines a difference (Cb-Ca) between the first particle concentration Ca and the second particle concentration Cb as a particle concentration of the particle component B.

Next, the calculation unit 180 displays the numbers of particles, the particle concentrations, the particle diameters, and the particle components of the particle components A and B on the display unit 187 (S182). The calculation unit 180 may output any or all of information of the numbers of particles, the particle concentrations, the particle diameters, and the particle components of the particle components A and B to the outside of the particle measuring apparatus 4. The gas to be measured is exhausted from the exhaust tube 199 to the outside of the particle measuring apparatus 4.

As described above, according to the fourth embodiment, the first and second liquid-containing units 110 and 112 are set to temperatures different from each other to set the gas flow passages 101 and 102 to degrees of supersaturation different from each other. In addition, the first and second optical detection units 140 and 142 detect particles in parallel temporally. According to this, the first and second optical detection units 140 and 142 can simultaneously detect particle components different from each other. For example, the first optical detection unit 140 detects the particle component A. Simultaneously, the second optical detection unit 142 can detect the particle components A and B. As a result, the particle measuring apparatus 4 according to the fourth embodiment can calculate the number of particles or the particle concentration, or the like of each of the particle components A and B in a short time.

In addition, the particle measuring apparatus 4 can simultaneously perform detection of particles under a plurality of temperature conditions without changing the temperature of the first and second liquid-containing units 110 and 112. Accordingly, even when the environment 100 temporally varies, the particle measuring apparatus 4 can detect a plurality of particle components contained in the environment 100 at a predetermined point of time.

In addition, in the fourth embodiment, the number of configurations such as the liquid-containing units which can be arranged in parallel between the environment 100 and the exhaust tube 199 is two sets. However, the number of the configurations such as the liquid-containing units may be three or greater sets. Any or all of the sets can include any of the components or configurations describe above, including a temperature adjustment tube. In this case, the particle measuring apparatus can simultaneously obtain numbers of particles and particle concentrations of three or more kinds of particle components (for example, A to C).

While certain embodiments have been described, these embodiments have been presented by way of example only, and are not intended to limit the scope of the present disclosure. Indeed, the embodiments described herein may be embodied in a variety of other forms; furthermore, various omissions, substitutions and changes in the form of the embodiments described herein may be made without departing from the spirit of the present disclosure. The accompanying claims and their equivalents are intended to cover such forms or modifications as would fall within the scope and spirit of the present disclosure. Moreover, some or all of the above described embodiments can be combined when implemented.

What is claimed is:
1. A particle measuring apparatus, comprising:
a first liquid container containing a liquid and provided at a periphery of a gas flow passage configured to allow a gas to pass;
a temperature controller configured to control a temperature of the first liquid container;
a first light source configured to irradiate the gas with light;
a first light detector configured to detect an intensity of reflected light from particles contained in the gas that passes through the first liquid container;

a first computer memory configured to store first data indicating a corresponding relationship between an aggregation temperature at which the liquid aggregates with the particles, and a particle component;

a second computer memory configured to store a number of particles or a particle concentration, which is detected by the first light detector, of the particles contained in the gas; and a processor configured to determine a component of the particles which are detected by the first light detector based on the temperature of the first liquid container, the first data, and the number of particles or the particle concentration, and further configured to calculate the number of particles or the particle concentration, wherein the temperature controller is configured to set the temperature of the first liquid container to a first temperature or a second temperature, each temperature corresponding to a different aggregation temperature, the second computer memory stores a first number of particles or a first particle concentration which is detected by the first light detector when the temperature of the first liquid container is the first temperature, the second computer memory is configured to store a second number of particles or a second particle concentration which is detected by the first light detector when the temperature of the first liquid container is the second temperature, and the processor is configured to set a difference between the first number of particles and the second number of particles, or a difference between the first particle concentration and the second particle concentration, as a number of particles or a particle concentration of a particle component corresponding to the second temperature.

2. The apparatus according to claim 1, further comprising:
a second liquid container containing a second liquid and provided at a periphery of a second gas flow passage configured to allow a second gas to pass;
a second light source configured to irradiate the second gas with light; and
a second light detector configured to detect an intensity of reflected light from particles contained in the second gas,
wherein the second aggregation temperature is different than the first aggregation temperature.

3. The apparatus according to claim 1, further comprising a first temperature adjustment tube provided at a periphery of the first liquid container, wherein the temperature controller is configured to control the temperature of the first liquid container by controlling a temperature of the first temperature adjustment tube.

4. The apparatus according to claim 3, wherein the first temperature adjustment tube includes an upper portion and a lower portion, and the temperature controller is configured to set the upper portion of the first temperature adjustment tube and the lower portion of the first temperature adjustment tube to different temperatures.

* * * * *